United States Patent [19]

Poole et al.

[11] Patent Number: 4,917,494

[45] Date of Patent: Apr. 17, 1990

[54] BEAM FORMING APPARATUS FOR AERODYNAMIC PARTICLE SIZING SYSTEM

[75] Inventors: Trent A. Poole, South Amherst; Norman C. Ford, Amherst, both of Mass.; Barton E. Dahneke, Palmyra, N.Y.

[73] Assignee: Amherst Process Instruments, Inc., Amherst, Mass.

[21] Appl. No.: 243,333

[22] Filed: Sep. 9, 1988

Related U.S. Application Data

[63] Continuation-in-part of Ser. No. 78,857, Jul. 28, 1987.

[51] Int. Cl.⁴ .................... G01N 15/14; G01N 21/85
[52] U.S. Cl. .................... 356/335; 350/169; 356/36
[58] Field of Search .......... 356/36, 335, 336, 338, 356/28; 250/564, 524, 222.2; 350/162.17, 162.22, 169; 377/40, 11, 53

[56] References Cited

U.S. PATENT DOCUMENTS 4,804,263  2/1989  Schodl ........................... 356/28

FOREIGN PATENT DOCUMENTS 7800453  8/1979  Sweden ........................... 356/28
463041   3/1975  U.S.S.R. ......................... 356/28

OTHER PUBLICATIONS

Blackford et al., "Particle Size Analysis with an Aerodynamic Particle Sizer ...", Proc. 11th Annual Powder & Bulk Solids Conf., Rosemont, IL, pp. 615–623, 5/86.

Primary Examiner—Davis L. Willis
Assistant Examiner—Matthew W. Koren
Attorney, Agent, or Firm—Wolf, Greenfield & Sacks

[57] ABSTRACT

Apparatus, intended primarily for use in an aerodynamic particle sizing system, for generating a pair of closely-spaced light beams, each having a thin, elongated cross-sectional shape. Particle sizes are determined by directing a particle stream through the light beams and measuring the times of flight of particles between the two light beams. The apparatus for generating the light beams includes a laser source and beam forming optics. In one embodiment, a first light beam is formed at the particle stream by a cylindrical lens. After passing through the particle stream, the first light beam is reflected and focused to form a second light beam at the particle stream that is displaced from the first light beam. The first light beam can be reflected and focused by a concave cylindrical mirror or, alternatively, by a flat mirror and a convex cylindrical lens. In another embodiment, the incident light beam from the laser source is passed through a diffraction grating which provides a zero order lobe and a first order lobe. The zero order lobe and the first order lobe are focused at a particle stream by a cylindrical lens to form the first and second beams.

22 Claims, 7 Drawing Sheets

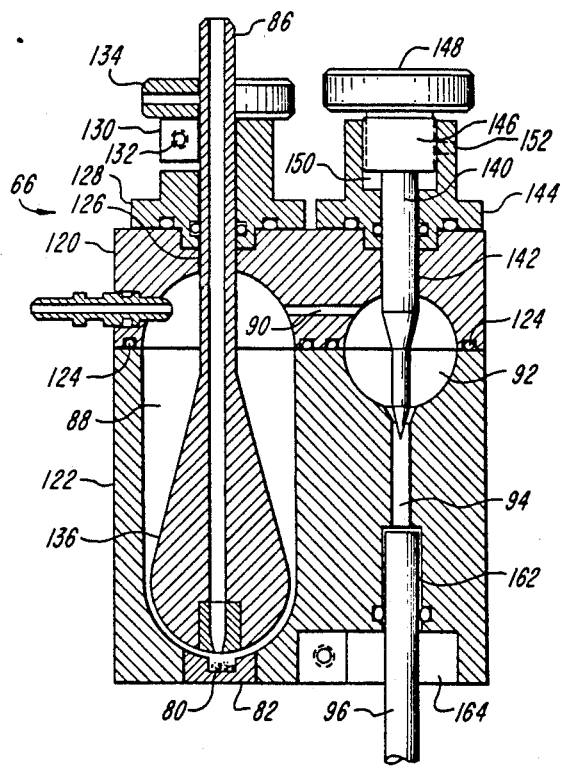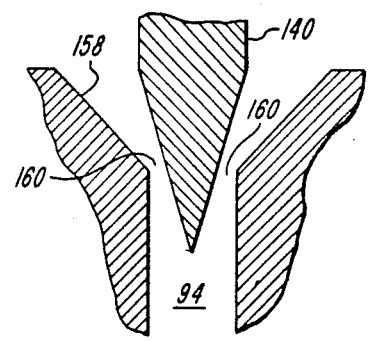
FIG. 6
FIG. 6A

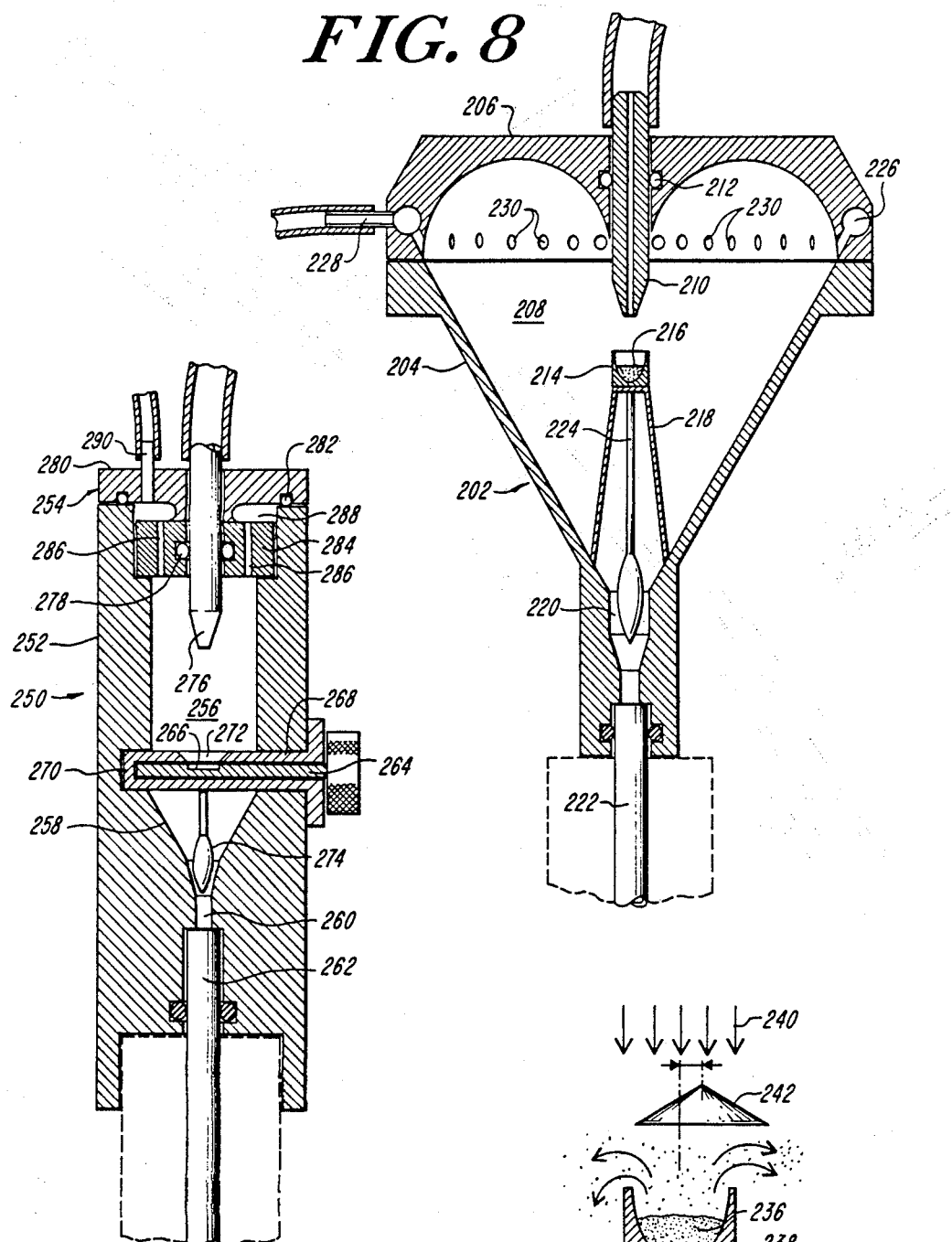

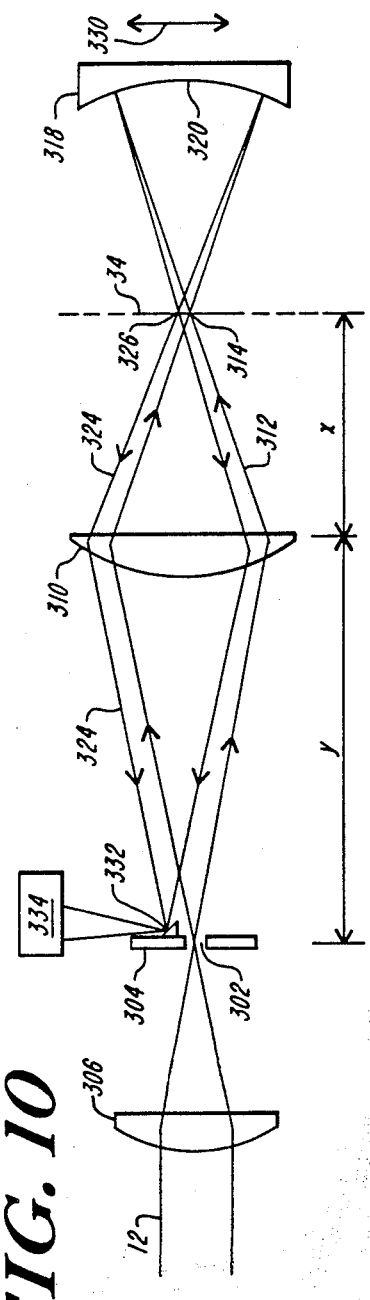
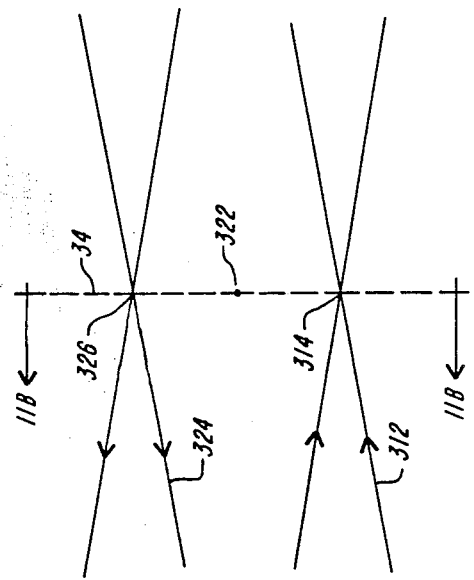
FIG. 10
FIG. 11A
FIG. 11B

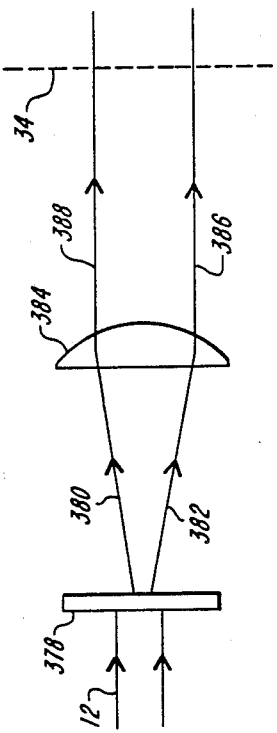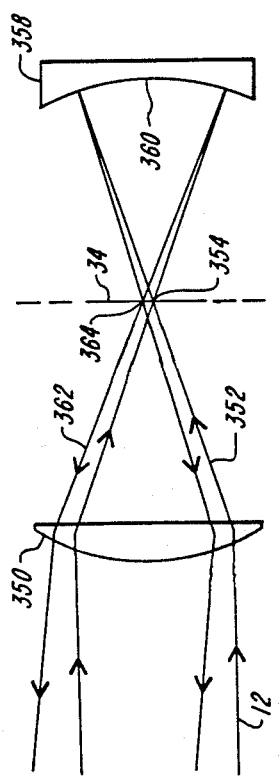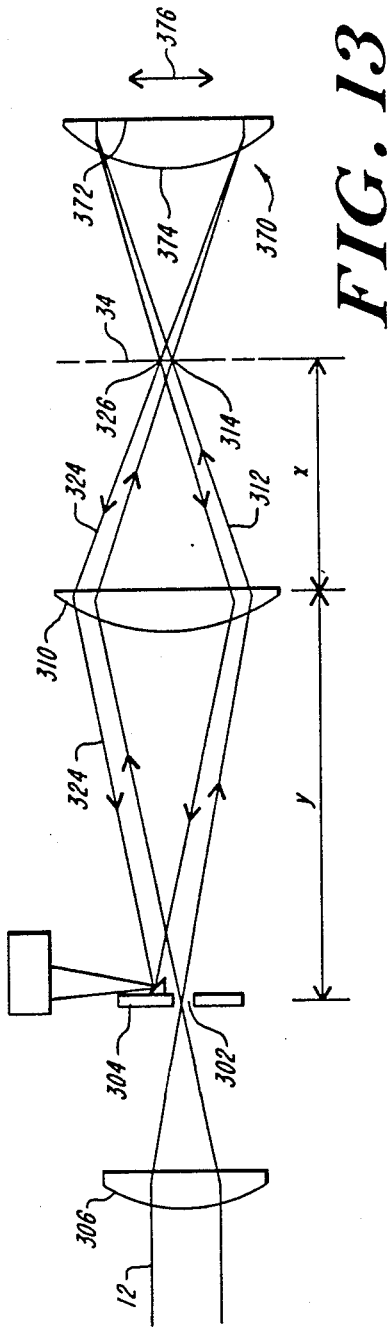

BEAM FORMING APPARATUS FOR AERODYNAMIC PARTICLE SIZING SYSTEM

CROSS-REFERENCE TO RELATED APPLICATION

This application is a continuation-in-part of application Ser. No. 078,857 filed July 28, 1987.

FIELD OF THE INVENTION

This invention relates to a time-of-flight system for measuring the sizes of particles and, more particularly, to apparatus for generating a pair of closely spaced light beams and for determining particle sizes by measuring the times of flight of particles between the two light beams.

BACKGROUND OF THE INVENTION

Powders composed of fine particles are utilized in one or more states of many industrial processes. Examples of such powders include food, pharmaceuticals, abrasives, pigments, plastics and magnetic coating materials. It is frequently desirable to measure the sizes of the particles in a powder. Another application of particle size measurement systems is for environmental analysis of airborne particulates such as smoke from industrial smoke stacks. Prior art techniques for measuring particle sizes have included sifting through meshes of various sizes, impingement of particles on piezoelectric devices, instruments wherein the particles are suspended in a liquid, light and electron microscopy, scattered light intensity measurements, light blockage measurements and instruments which utilize Fraunhofer diffraction patterns. Prior art particle size measurement systems have been restricted by a variety of disadvantages. Some have an inability to measure particles in the micron and submicron size range, others lack resolution between particles of different sizes and still others have an inability to measure a variety of particle types. For example, the instrument wherein particles are suspended in a liquid for measurement by Coulter principle or sedimentation is useless for particles that dissolve in or chemically react with that liquid.

A technique for particle size measurement utilizing a time-of-flight technique is disclosed in U.S. Pat. No. 3,854,321 issued Dec. 17, 1974 to Dahneke. An aerosol containing the particles to be measured is accelerated through a nozzle and is injected through two spaced-apart beams of light in a vacuum chamber. As a particle passes through each light beam, light scattering occurs. A detector receives a scattered light pulse from the first beam and from the second beam for each particle. The time delay between pulses represents particle velocity which is directly related to particle size. The time-of-flight technique for particle size measurement is also disclosed by D. B. Blackford et al "Particle Size Analysis With An Aerodynamic Particle Sizer", Proceedings of the 11th Annual Powder and Bulk Solids Conference, Rosemont, Ill., pp. 615–623, May 12–15, 1986 and J. K. Argarwal et al "An Instrument For Real Time Aerodynamic Particle Size Analysis Using Laser Velocimetry", Proceedings of The Inhalation, Toxicology and Technology Symposium, ed. by Basil K. J. Leong, Ann Arbor Science Publishers, 1981, pp. 207-231. The output of such an instrument is typically a distribution of the number of particles measured at each particle size over a range of sizes.

The time of fliqht technique has in the past suffered from various disadvantages. It is desirable in the time-of-flight technique to utilize a supersonic flow of particles through the measurement region. When the flow is supersonic, the particle velocity is independent of pressure variations in the air source. However, in practical nozzle configurations, supersonic flow occurs only over a distance of 2 to 3 millimeters from the end of the nozzle. Thus, the two light beams utilized to measure particle velocity must be spaced on the order of about one millimeter. Conventional beam splitting techniques utilizing partially transmissive mirrors are impractical and difficult to align for such closely-spaced beams. A calcite plate has also been utilized for splitting a beam into two closely-spaced components (see Argarwal et al publication referenced hereinabove). However, the calcite plate produces output beams with different polarizations. This is undesirable since light scattering by particles will be different for the two beam polarizations.

Another difficulty with prior art time-of-flight particle size measurement systems has been detection of the two closely-spaced light beams. It is desirable to separately detect the two beams so that start and stop pulses are automatically identified. However, it is physically difficult to position separate detectors only one millimeter apart. Optical fibers can be utilized to conduct the light beams to remotely located detectors. However, a significant portion of the scattered light is reflected from the end face of each optical fiber.

A further difficulty with prior art time-of flight particle size measurement systems relates to the injection of particles through the two light beams for measurement. Samples to be measured are often in the form of a powder sample which is an agglomeration of particles that are usually in clusters due to attraction by electrostatic forces. In order to accurately measure the particles using the time-of-flight technique, the clusters must be separated into individual particles and carried by air, one at a time, as a particle stream through the measurement chamber. Clearly, if clusters of particles pass through the measurement chamber, individual particles cannot be measured. In addition, particles in an aerosol tend to stick to the walls of any container through which they pass.

It is a general object of the present invention to provide an improved particle size measurement system.

It is another object of the present invention to provide apparatus for generating closely-spaced first and second light beams in an image plane, each light beam having a relatively thin, elongated cross sectional shape.

It is yet another object of the present invention to provide apparatus for generating closely spaced first and second light beams that have the same polarization.

It is still another object of the present invention to provide apparatus for generating closely spaced first and second light beams wherein the spacing between light beams can be accurately controlled.

It is still another object of the present invention to provide a particle sizing system incorporating the above features.

SUMMARY OF THE INVENTION

According to the present invention, these and other objects and advantages are achieved in apparatus for generating closely-spaced first and second light beams in an image plane, each light beam having a thin, elongated cross-sectional shape. The apparatus comprises source means for generating an incident light beam, means defining an aperture slit, first lens means for focusing the incident light beam on the slit-defining means, second lens means positioned for focusing an image of the aperture slit in the image plane to form the first light beam, and optical means for reflecting the first light beam after it passes through the image plane to form a reflected first light beam and for focusing the reflected first light beam in the image plane to form the second light beam spaced from the first light beam.

In a preferred embodiment, the optical means comprises a concave cylindrical mirror having an axis lying in the image plane between the first and second light beams. In another preferred embodiment, the optical means comprises a flat mirror and a convex cylindrical lens. The cylindrical lens is spaced from the image plane by a distance equal to its focal length. In either embodiment of the optical means, the apparatus preferably includes adjustment means for adjusting the spacing between the first and second light beams. The adjustment means includes means for displacing the optical means in a plane parallel to the image plane. The first lens means and the second lens means each typically comprise a cylindrical lens.

According to another aspect of the present invention, apparatus for generating closely-spaced first and second light beam in an image plane, each light beam having a thin, elongated cross-sectional shape comprises source means for generating an incident light beam, a cylindrical lens for focusing the incident light beam in the image plane to form the first light beam, and optical means for reflecting the first light beam after it passes through the image plane to form a reflected first light beam and for focusing the reflected first light beam in the image plane to form the second light beam spaced from the first light beam.

According to still another aspect of the invention, a method for generating closely-spaced first and second light beam in an image plane, each light beam having a thin, elongated cross-sectional shape comprises the steps of generating an incident light beam, focusing the incident light beam on an aperture slit, focusing an image of the aperture slit in the image plane to form the first light beam, reflecting the first light beam after it passes through the image plane to form a reflected first light beam, and focusing the reflected first beam in the image plane to form the second light beam spaced from the first light beam.

According to a further aspect of the invention, a particle sizing system comprises an evacuated measurement chamber, means for directing a stream of particles to be measured through the measurement chamber, beam generating means for directing closely-spaced first and second light beams through the particle stream, each light beam having a thin cross-section along the direction of the particle stream and having an elongated cross-section in a direction perpendicular to the particle stream, and means for measuring particle sizes based on the times of flight of particles in the particle stream between the first light beam and the second light beam. The beam generating means includes source means for generating an incident light beam, means defining an aperture slit, first lens means for focusing the incident light beam on the slit-defining means, second lens means positioned for focusing an image of the aperture slit at the particle stream to form the first light beam, and optical means for reflecting the first light beam after passing through the particle stream to form a reflected first light beam and for focusing the reflected first light beam at the particle stream to form the second light beam spaced from the first light beam.

According to a further aspect of the invention, apparatus for generating closely spaced first and second light beams in an image plane, each light beam having a thin, elongated cross-sectional shape comprises source means for generating an incident light beam, a diffraction grating positioned to convert a portion of the light beam into diffracted beams in a zero order lobe and at least one first order lobe, and a cylindrical lens spaced from the diffraction grating for focusing the zero order lobe and the first order lobe into the first and second light beams, respectively. The cylindrical lens is spaced from the diffraction grating such that the first and second light beams are substantially parallel.

BRIEF DESCRIPTION OF THE DRAWINGS

For a better understanding of the present invention together with other and further objects, advantages and capabilities thereof, reference is made to the accompanying drawings which are incorporated herein by reference and in which:

FIG. 6 is a cross-sectional view of the powder disperser of FIG. 4;

FIG. 6A is an enlarged cross-sectional view of the outlet region of the powder disperser of FIG. 6;

FIG. 8 is a cross-sectional view of another embodiment of a powder disperser;

FIG. 8A illustrates another technique for agitating the powder sample;

FIG. 9 is a cross-sectional view of still another embodiment of a powder disperser;

FIG. 10 is a schematic diagram of another embodiment of the beam forming optics;

FIG. 11A is an enlarged, partial schematic diagram of the particle stream and the dual light beams;

FIG. 11B is an enlarged, partial schematic diagram of the particle stream and the dual light beams taken along the line 11B—11B of FIG. 11A;

FIG. 12 is a schematic diagram of still another embodiment of the beam forming optics;

FIG. 13 is a schematic diagram of a further embodiment of the dual beam forming optics; and FIG. 14 is a schematic diagram of yet another embodiment of the beam forming optics.

DETAILED DESCRIPTION OF THE INVENTION

Figure 1:
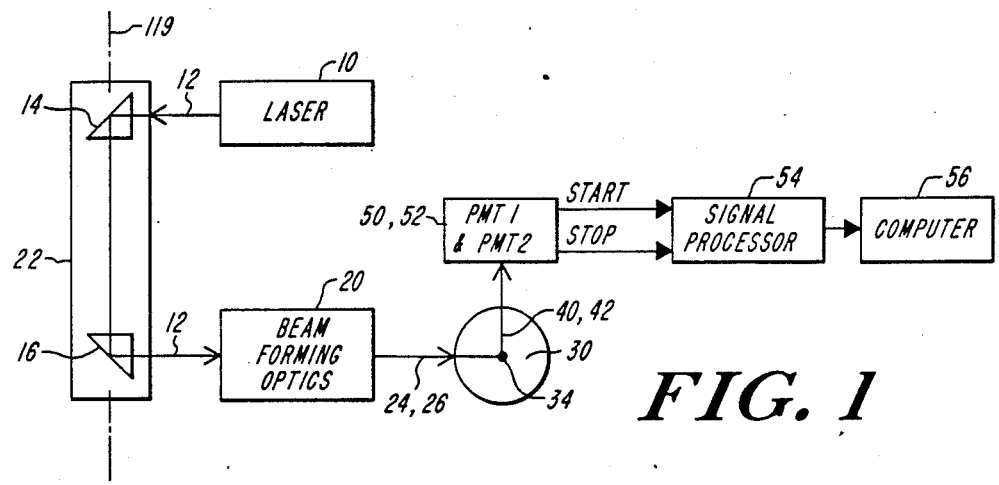
FIG. 1 is a block diagram of a particle size measurement system in accordance with the present invention.
Figure 2:
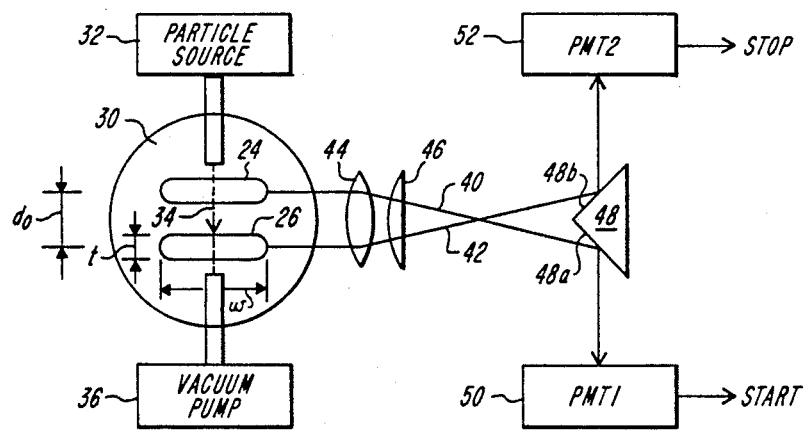
FIG. 2 is a partial block diagram of the particle size measurement system as viewed along the axis of the laser measurement beam.

An aerodynamic particle sizing system in accordance with the present invention is shown in block diagram form in FIGS. 1 and 2. A laser 10 generates a light beam 12 which is reversed in direction by prisms 14 and 16 and is directed at beam forming optics 20. A suitable laser 10 is of the helium neon gas laser type that produces an output at a wavelength of 6328 Angstroms. The light beam 12 is reversed in direction simply to provide a more compact unit. The prisms 14 and 16 are mounted on a metal frame 22 which permits adjustment of the beam 12 as described hereinafter. The beam forming optics 20 produce a pair of closely-spaced light beams 24 and 26 (FIG. 2) which enter a measurement chamber 30. Each of the light beams 24, 26 has a thin, elongated shape as shown in FIG. 2. In one exemplary system, the spacing $d_o$ between beams 24 and 26 is on the order of about 1 millimeter, and each of the beams 24, 26 has a width w of about 1 millimeter and a thickness t of about 0.03 millimeter. The disclosed system is suitable for measuring particles in the size range between 0.3 and 100 micrometers.

As shown in FIG. 2, a particle source 32 injects a particle stream 34 into the measurement chamber 30 and through beams 24 and 26. The particles are then evacuated from the chamber 30 by a vacuum pump 36. As a particle passes through each of the beams 24, 26, light is scattered and forms scattered light beams 40 and 42, respectively. When light beams 24, 26 are very thin, the scattered light beams 40 and 42 each consist of a brief pulse of light. The scattered light beams 40, 42 which are perpendicular to the direction of beams 24 and 26, pass through a focusing lens 44 and impinge on two faces of a prism 48. Lens 44 should have as large an aperture as possible, and is typically an f1.7 aperture. Prism faces 48a and 48b are perpendicular to each other. The prism faces 48a and 48b reflect scattered light beams 40 and 42 in opposite directions to photomultiplier tubes 50 and 52, respectively, which are each directed at one face of the prism 48.

In another embodiment, focusing lenses 44, 46 are replaced by a concave mirror (not shown) for imaging scattered light on prism faces 48a and 48b. The mirror is located on the opposite side of the measurement chamber 30 from the prism 48.

The photomultiplier tubes 50 and 52 produce START and STOP pulse output signals, respectively, representative of the received scattered light beams 40 and 42. When a particle in particle stream 34 passes through light beam 24, a START pulse is provided by photomultiplier tube 50; and when the particle passes through light beam 26, a STOP pulse is provided by photomultiplier tube 52. The time delay between the START and STOP pulses represents time for the particle to travel between light beam 24 and light beam 26. The START and STOP pulses are supplied to a signal processor 54 (FIG. 1) which measures the time of fliqht for each particle in particle stream 34. The number of particles measured at each time of flight in a prescribed range is temporarily stored in the signal processor 54. The time of fliqht information is forwarded by the signal processor 54 to a computer 56 which processes the time of flight data to determine particle sizes and to provide selected displays and printouts. Typically, a particle size distribution is the format required by a user.

Figure 3:
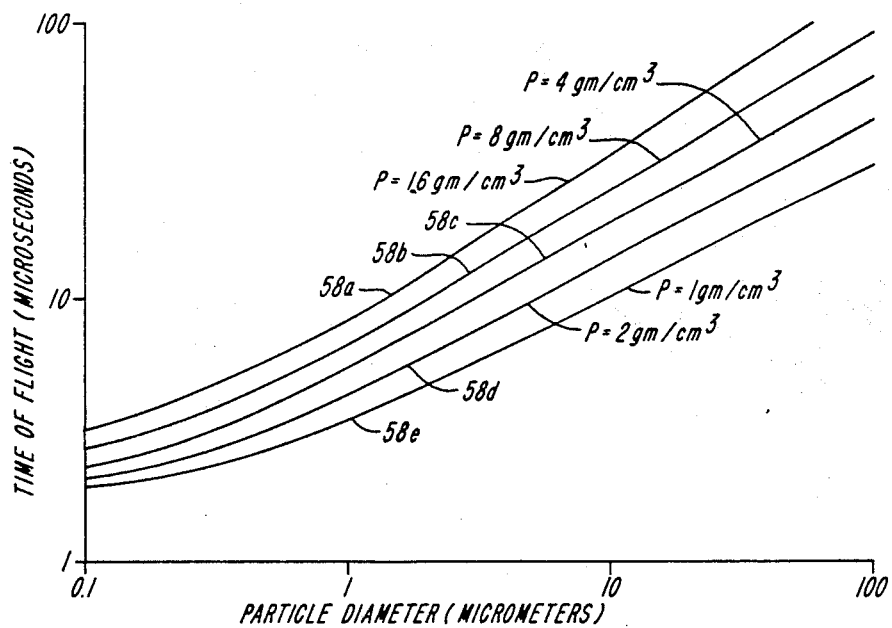
FIG. 3 is a graph illustrating the time of flight of particles as a function of particle diameter for various particle densities.

A plot of time of flight in microseconds as a function of particle diameter in micrometers for the system of FIGS. 1 and 2 is shown in FIG. 3. For the plot shown, the spacing between light beams is 1.14 millimeter. Curves 58a, 58b, 58c, 58d and 58e represent particles of different densities. For a given particle density, the time of flight is a monotonically increasing function of particle diameter. Thus, an nonambiguous particle size measurement can be obtained. Using the curves 58a, 58b, 58c, 58d and 58e, particle size can be determined from the measured time of flight. It has been found that a supersonic gas and particle flow through the measurement chamber 30 produces a time of flight which is essentially independent of the pressure at which the particle source 32 injects particle stream 34 into the chamber 30, provided the chamber pressure is less than 0.1 atmosphere.

Figure 4:
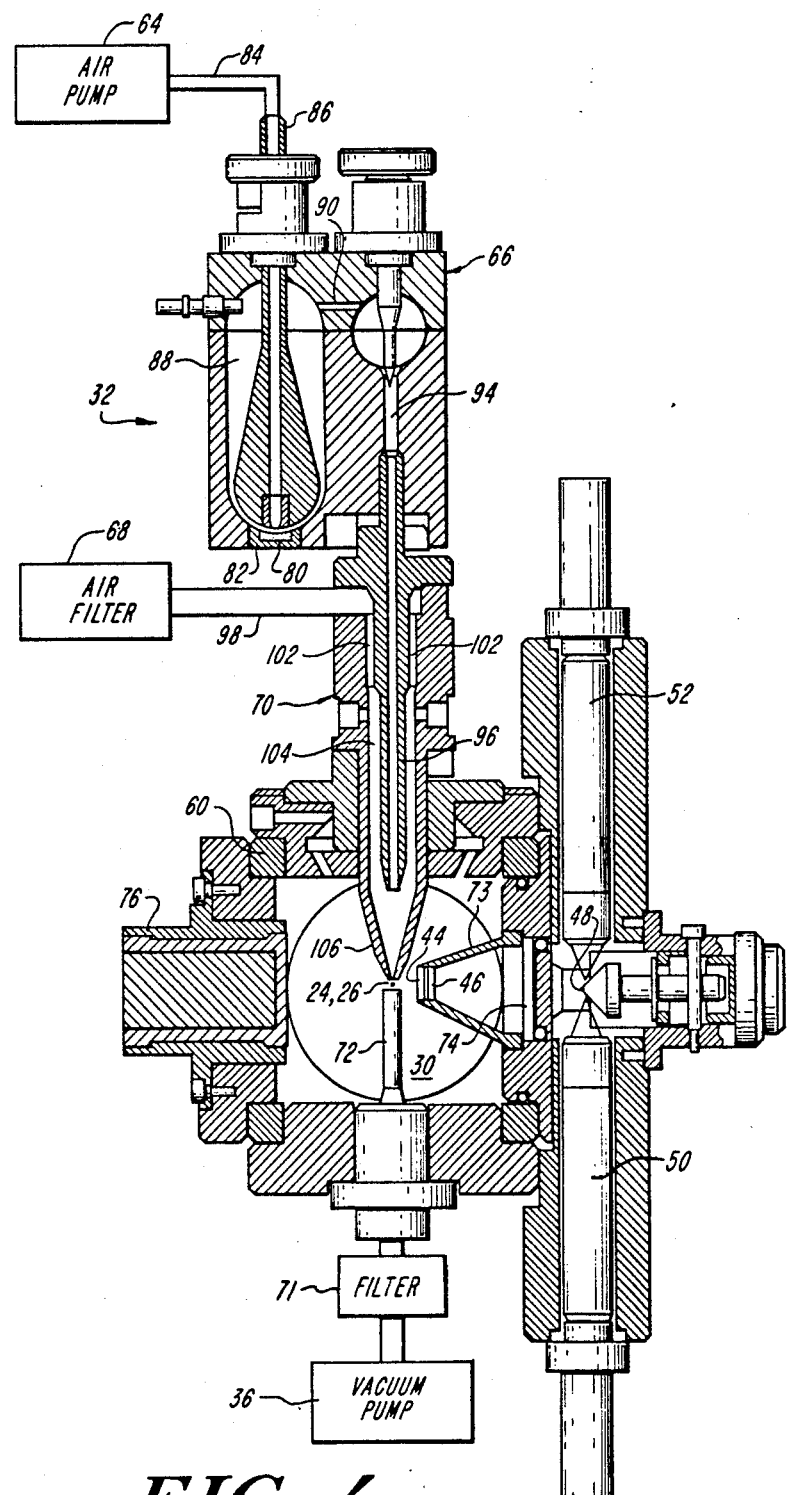
FIG. 4 is a cross-sectional view of a particle size measurement system in accordance with the present invention taken through the measurement chamber and powder disperser.

A cross sectional view, partly schematic, of the particle size measurement system is shown in FIG. 4. The measuring light beams 24, 26 are perpendicular to the paper. The measurement chamber 30 is defined by a housing 60 which is generally cube shaped and which has openings on each of the six cube faces for access to the measurement chamber 30. The particle source 32, comprising an air pump 64, a powder disperser 66 and a nozzle assembly 70, is connected to measurement chamber 30 through an opening in the top face of housing 60. The vacuum pump 36 and a filter 71 are connected by a conduit 72 through an opening in the bottom face of the housing 60 to measurement chamber 30. The photomultiplier tubes 50 and 52 and prism 48 are mounted to the right side of housing 60. The prism 48 is adjustable to permit alignment of the scattered light beams 40, 42 with the photomultiplier tubes 50, 52, respectively. Lenses 44 and 46 are mounted in the chamber 30 adjacent to the beams 24, 26 by a mounting bracket 73 which is attached to housing 60. Scattered light beams 40, 42 pass through lens 44 and impinge on the prism 48 as described hereinabove. A plug 76 closes an opening in the left side wall of the housing 60. The light beams 24, 26 enter the measurement chamber 30 through an opening in the rear wall of housing 60.

A powder sample 80 is placed in a sample holder 82 in powder disperser 66. Air pump 64 is connected by a conduit 84 to an inlet tube 86 which extends into a first chamber 88 in powder disperser 66. Air is pumped through the tube 86 and agitates the powder sample 80, producing a cloud of particles in first chamber 88. The particle cloud is carried by the air flow through a passageway 90 connecting first passage 88 and a second chamber 92. The second chamber 92 includes means for separating clusters of particles which may be stuck together due to electrostatic forces. The detailed operation of the powder disperser 66 is described hereinafter. The particle stream passes through an outlet 94 of the powder disperser 66 and through a sample injection tube 96 into nozzle assembly 70.

An air filter 68 is connected by a conduit 98 to the upper portion of the nozzle assembly 70 which contains tubular passages 102 surrounding sample injection tube 96. Air is drawn through filter 68, conduit 98 and passages 102 to an annular space 104 surrounding the lower portion of sample injection tube 96. Annular space 104 is defined between injection tube 96 and an outer nozzle 106. Injection tube 96 terminates inside outer nozzle 106, while outer nozzle 106 extends into measurement chamber 30. The tip of injection tube 96 is about ⅜ inch back from the tip of outer nozzle 106. The tip of outer nozzle 106 is tapered inwardly and has a generally conical shape.

In operation, the stream of particles is fed through sample injection tube 96 while clean air passes through annular space 104 to form a sheath of clean air around the stream of particles entering the measurement chamber 30. The stream of particles passes through the two closely-spaced light beams as described hereinabove and is then evacuated from the measurement chamber 30 by vacuum pump 36. The particles are removed from the air stream by filter 71 to avoid clogging and contamination of vacuum pump 36.

It has been found that when the tip of conduit 72 is spaced from the tip of outer nozzle 106 by a distance of about ¼ inch, efficient evacuation of measurement chamber 30 is provided. The flow of gas from nozzle 106 into conduit 72 entrains gas molecules from chamber 30 in the flow and produces a pressure in chamber 30 which is substantially lower than the pressure at the input to vacuum pump 36. As a result, the system can be operated with a vacuum pump 36 having a lower pumping capacity than otherwise would be required. Typically, the vacuum pump 36 can have a pumping capacity on the order of 6 liters per minute at STP while maintaining a pressure of 0.1 atmosphere. In one example, the pressure in the chamber 30 was 0.067 atmosphere, while the pressure at the inlet to vacuum pump 36 was 0.115 atmosphere.

Figure 5:
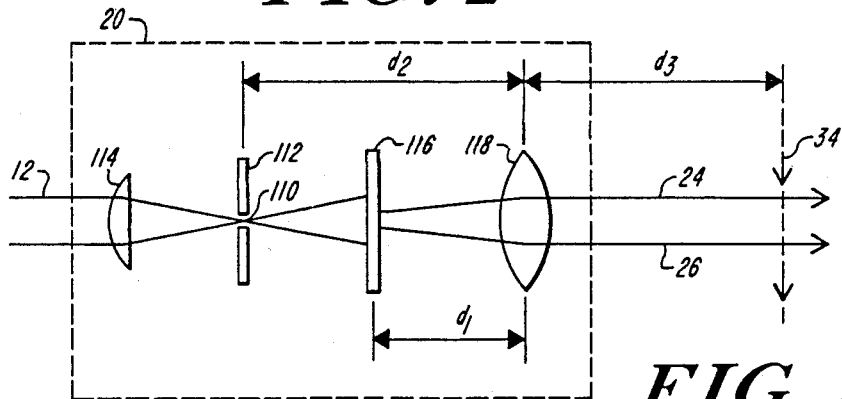
FIG. 5 is a schematic diagram of the dual beam forming optics shown in FIG. 1.

The beam forming optics 20 for converting laser beam 12 from the laser 10 into the dual closely-spaced light beams 24 and 26 are illustrated in FIG. 5. The laser beam 12 is focused on a slit aperture 110 in an aperture plate 112 by a cylindrical lens 114. The slit aperture 110 preferably has a width of about 0.1 millimeter and a length of about 3 millimeters and is used as a spatial filter to block off-axis portions of laser beam 12. The cylindrical lens 114 is used to focus the beam 12 on the elongated slit aperture 110. The beam diverging from the slit aperture 110 impinges on a diffraction grating 116 constructed so that most of the input light energy appears in the zero order lobe and one of the first order lobes. Techniques for concentrating the light energy in the zero order lobe and one first order lobe are known in the art. The technique is commonly known as "blazing." In a preferred embodiment, the grating has 70 lines per millimeter.

The output beams from the diffraction grating 116 are directed at a lens 118. The spacing $d_1$ between the lens 118 and the diffraction grating 116 is approximately equal to the focal length of lens 118 so that the two beams 24, 26 are rendered substantially parallel to each other. The beams 24 and 26 are then directed into the measurement chamber 30 across the particle stream 34. The distance $d_3$ between the lens 118 and particle stream 34 and the distance $d_2$ between the lens 118 and slit aperture 110 are selected so that the slit aperture 110 is sharply imaged at particle stream 34. In a preferred embodiment, spacing $d_1$ is approximately 5 millimeters and spacings $d_2$ and $d_3$ are each approximately 10 millimeters.

The beam forming optics 20 provide substantially parallel beams 24 and 26 which have the same polarization as the laser 10 and which are extremely thin in the direction of the particle stream 34. As a result, a high resolution time-of-flight measurement can be obtained. In order to obtain an accurate time of flight measurement, the spacing between beams 24 and 26 must be carefully controlled. In the beam forming optics 20 shown in FIG. 5, the beam spacing is a function of the distance $d_1$ which can be accurately established. Minor variations in $d_1$ due to temperature changes or vibration of the instrument do not produce significant variations in the spacing between beams 24 and 26. Furthermore, the beam spacing can be varied or accurately adjusted by varying the position of diffraction grating 116 along the beam axis. The beams 24 and 26 go slightly out of parallel, but the beam spacing is most critical to time-of-flight measurements.

As noted above, the prisms 14 and 16, which reverse the direction of laser beam 12, are mounted on a metal frame 22. By using a single-piece machined frame 22, the relative orientations of prisms 14 and 16 can be accurately established. In addition, the laser beam 12 can be aligned with the beam forming optics 20 by movement of the frame 22. Preferably, the beam 12 is aligned in two dimensions by rotation of the frame 22 about an axis 119 (FIG. 1) and by movement of the frame 22 parallel to axis 119.

The powder disperser 66 will be described with reference to FIG. 6. An upper body member 120 and a lower body member 122 are provided with aligned cavities which together define first chamber 88. Similarly, body members 120 and 122 are provided with aligned cavities which define second chamber 92. The upper and lower body members can be fabricated from plastic, metal or other suitable material and are joined together with conventional mounting hardware (not shown) and sealed with O-rings 124.

The upper body member 120 is provided with an opening 126 for inlet tube 86. A bushing 128, mounted to the exterior of body number 120 in alignment with opening 126, provides support for tube 86. The upper portion of bushing 128 is provided with portions 130 having sufficient flexibility to grip tube 86 when they are urged together by an adjustment screw 132. The tube 86 is provided with a knob 134. When the screw 132 is loosened, the tube 86 can be moved axially in bushing 128 to a desired position. The screw 132 is then retightened to fix the tube 82 at the desired position.

The end of the tube 86 within first chamber 88 has an enlarged and rounded end portion 136 which avoids any sharp corners which can otherwise cause particle deposition. The tip of tube 86 is restricted to a prescribed, very small orifice, for example, 0.005-inch, to provide a jet of relatively high speed air just above the sample 80. When air is supplied through the tube 86, the jet of air agitates the sample 80 and produces a cloud of particles in first chamber 88. The position of the tube 86 can be varied along its axis as described above, to provide a desired amount of agitation of the sample 80. The interior of first chamber 88 has rounded surfaces in order to avoid any sharp corners which encourage particle deposition. The bushing 128 and the tube 86 are sealed to the powder disperser 66 by suitably located O-rings.

The cloud of particles in first chamber 88 flows through the passageway 90 to the second chamber 92. The passageway 90 has a small cross-sectional area, preferably on the order of 1/16 inch, to maintain a high velocity air flow and thereby prevent deposition of particles. A needle, or pin 140, passes through an opening 142 in upper body member 120 into second chamber 92. The pin 140 extends through second chamber 92 and terminates in outlet 94. The pin 140 is retained in position by a bushing 144 mounted to the exterior of upper body member 120 in alignment with opening 142. A threaded collar 146 and a knob 148 are attached to the end of pin 140 outside chamber 92. The bushing 144 is provided with a cup-shaped recess 150 having threads on its inner wall which engage the threads on collar 146. Thus, when knob 148 is turned, the pin 140 is caused to move axially inward or outward in the second chamber 92, and in particular, to move relative to the outlet 94 as described hereinafter. A set screw 152 permits pin 142 to be locked in position.

An enlarged view of outlet 94 of powder dispenser 66 and the tip of pin 140 is shown in FIG. 6A. The entrance to outlet 94 from second chamber 92 is provided with a tapered wall portion 158 having a truncated conical shape. The tip of pin 140 is tapered inwardly to provide a generally conical or pointed shape. The taper of the wall portion 158 and the tip of pin 140 are preferably different. As a result, when pin 140 is moved into proximity to outlet 94, an annular region 160 of restricted air flow is created. Particles and clusters of particles passing through the annular region 160 are subjected to relatively high shear forces. As a result, particle clusters are separated into individual particles as they pass through the annular region 160, and the particle stream at the outlet 94 consists essentially of single particles. The sample injection tube 96 extends into an opening 162 in lower body member 122. The lower body member 122 is further provided with a recess 164 for mounting the powder disperser 66 to the nozzle assembly 70.

In operation, a source of air is connected to inlet tube 86 and air flow through the tip of tube 86 causes agitation of the powder sample 80 into a cloud of particles in first chamber 88. The air flow carries the cloud of particles through passageway 90 to second chamber 92, and then carries the particles through the narrowed annular region 160 where they are subjected to shear forces that tend to separate clusters of particles. The stream of particles then passes through the outlet 94 and into the nozzle assembly 70. The axial adjustability of inlet tube 86 permits control over the agitation of powder sample 80, while the axial adjustability of pin 140 permits precise control over the annular shear region 160. The pin 140 can be varied in position between a closed condition and a fully open condition, depending on the size of the particles in the sample 80 and the tendency for the particles to stick together. Axial movement of pin 140 causes a variation in size of the annular orifice corresponding to annular region 160. In a preferred embodiment, air is supplied through the tube 86 at a pressure of approximately 15 psi.

While the powder disperser 66 has been described primarily in connection with the particle size measurement system shown in FIGS. 1-5, it will be understood that the powder disperser 66 can be utilized in any system requiring the formation of a stream of particles from a powder sample. Furthermore, the rate of air flow and the dimensions of the passageway and the annular region 160 can be varied to accommodate a wide variety of particle types and sizes.

Figure 7:
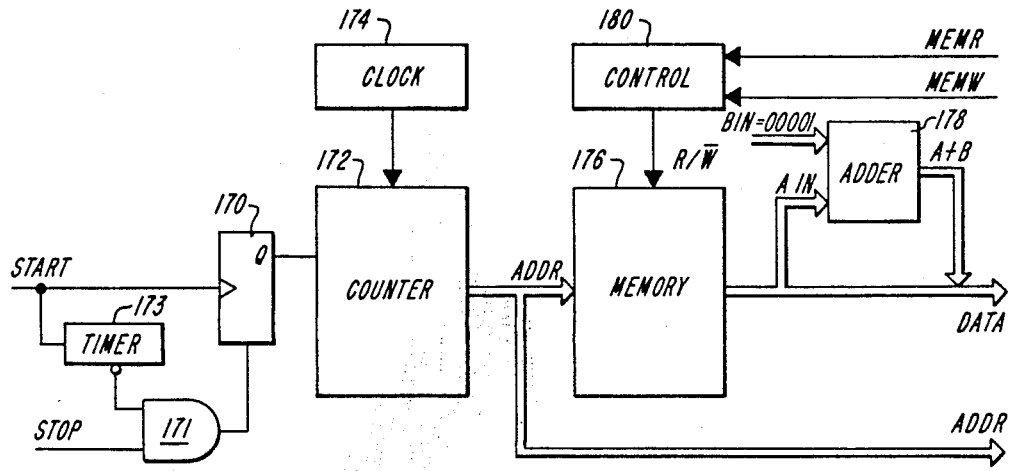
FIG. 7 is a schematic block diagram of the signal processor shown in FIG. 1.

A block diagram of the signal processor 54 is shown in simplified form in FIG. 7. The START pulse from photomultiplier tube 50 is coupled to the toggle input of a flip flop 170, and the STOP pulse from photomultiplier tube 52 is coupled to one input of a gate 171. A timer 173 which is initiated by the START pulse has its active low output coupled to another input of gate 171. The output of gate 171 is coupled to the clear input of flip flop 170. The Q output of flip-flop 170 is at a high logic level during the time between the START and STOP pulses, and is coupled to the enable input of a digital counter 172. A digital clock 174, typically having an output frequency of 40 MHz, is coupled to the clock input of counter 172. The counter 172 is permitted to accumulate counts during the time between the START and STOP pulses. The count value represents time of flight of the particle between beams 24 and 26.

The gate 171 and the timer 173 prevent flip-flop 170 from being cleared for a prescribed time interval, determined by timer 173, after the START pulse. The timer 173 inhibits the gate 171 during the prescribed time interval. The purpose of this circuit is to reduce false measurements due to noise and STOP pulses originating from particles other than the one being measured, based on the fact that at least the prescribed time interval is required for a particle to travel between light beams 24 and 26.

The output of counter 172 which, for example, may be 11 bits, is used to address a random access memory 176. Each location in the memory 176 represents one time of flight value and, hence, one particle size. The entire memory 176 represents a range of particle sizes. The data output of the memory 176 is coupled to the A input of a digital adder 178. A binary value of one is coupled to the B input of adder 178. When a particle time of flight is recorded by counter 172 and the appropriate location in memory 176 is addressed, one count is added to the number stored in that location by adder 178, and the incremented number is returned to the same memory location. As a result, the memory 176 stores the number of particles measured for each particle size in the range of interest.

Data in the memory 176 can be transferred to the computer 56 by conventional means for data logging and display. A control unit 180 controls reading and writing of information to and from memory 176. As described above, the appropriate memory location is incremented by one after each particle is measured. Alternatively, reading and writing of data can be performed under control of computer 56 on the data and address busses and by control signals MEMR and MEMW supplied from computer 56. An alternative embodiment of the signal processor 54 is a digital correlator such as an LFI Model 1096.

Another embodiment of a powder disperser is shown in FIG. 8. A container 202 includes a generally conical lower body member 204 having a conical interior cavity, and an upper body member 206 having an annular interior cavity. When the upper and lower body members 204, 206 are attached together, an interior chamber 208 is defined by the respective cavities. Preferably, the conical portion of chamber 208 has a half angle of about 30°. An inlet tube 210 extends through a hole in the center of upper body member 206 and is sealed by an O-ring 212. A sample cup 214 for holding a powder sample 216 is supported in the center part of chamber 208 by a tripod strut assembly 218 comprising three relatively thin, elongated support legs extending to the wall of lower body member 204. An outlet 220 from the powder disperser leads to a sample injection tube 222. A pin 224 extends downwardly from sample cup 214 and terminates in the outlet 220. The lower end of pin 224 is tapered so that the pin 224 and outlet 220 together define an annular shear region between them, as shown in FIG. 6A and described hereinabove.

The upper body member 206 is provided with a circumferential passage 226 with an inlet tube 228 for connection to an air supply. The passage 226 is in gas communication with a plurality of spaced-apart holes 230, distributed around the periphery of the interior cavity in upper body member 206. When air is supplied through inlet tube 228, the air flows uniformly through holes 230 into the chamber 208 as a sheath of air as described hereinafter.

In operation, a flow of air is supplied through tube 210 directly onto powder sample 216 so as to agitate the sample and produce a cloud of particles as described hereinabove in connection with FIG. 6.

In addition, the air flow produces a vibration of the sample cup 214, since it is supported by the elongated legs of strut assembly 218. The vibration causes a further agitation of powder sample 216 and assists in breaking up the powder sample and producing a cloud of particles. At the same time, air is supplied through inlet tube 228 and holes 230 to create a sheath of air around the periphery of chamber 208. The clean air sheath flows from holes 230 toward outlet 220 along the chamber 208 walls and inhibits deposition of particles on walls of the chamber 208. In addition, the interior walls of chamber 208 avoid sharp corners which can promote air turbulence and deposition of particles. The upper portion of chamber 208 is smoothly curved, while the lower portion has a conical shape. The cloud of particles flows through chamber 208 toward outlet 220 and passes through the annular shear region, causing clusters of particles to be separated, as described hereinabove in connection with FIG. 6. The resulting stream of particles passes through outlet 220 and sample injection tube 222 to the particle size measurement system or other instrument.

A modification of the powder disperser is shown in FIG. 8A. A powder sample 236 is located in a sample cup 238 in one of the powder dispersers described herein. An air flow 240 is directed at the powder sample 236 from above. A conical cap 242 is spaced above sample cup 238 with the apex of the cone facing air flow 240 and offset from the center of sample cup 238. The cap 242 produces turbulence in the region of powder sample 236 and causes swirl-induced discharge of the powder sample from the sample cup 238 to produce a cloud of particles.

Another embodiment of a powder disperser is shown in FIG. 9. A container 250 includes a generally cylindrical body member 252 and a removable cover 254. The body member 252 and cover 254 together define a generally cylindrical chamber 256 having a tapered lower portion 258 leading to an outlet 260 and a sample injection tube 262. A sample tray 264 containing a powder sample 266 is inserted through an opening 268 in body member 252 into chamber 256. The sample tray 264 is retained in position by a sample tray guide 270 having an aperture 272 which exposes the powder sample 266. The sample tray 264 and sample tray guide 270 extend across the chamber 256 for support by both sides of body member 252. However, the tray 264 and guide 270 have a narrow width dimension to permit air flow around these elements to outlet 260. A pin 274 extends downwardly from sample tray guide 270 to outlet 260 and has a tapered tip for producing an annular shear region as described hereinabove in connection with FIG. 6A.

An inlet tube 276 extends through an opening in cover 254 and is sealed to cover 254 by an O-ring 278. Cover 254 includes an upper portion 280 sealed to body member 252 by an O-ring 282 and a lower portion 284 having a series of axial passages 286. A space 288 is defined between upper portion 280 and lower portion 284. The passages 286 interconnect space 288 and chamber 256. An inlet tube 290 passes through upper portion 280 and connects to space 288.

In operation, powder sample 266 is placed in the disperser in sample tray 264. A jet of air is supplied through tube 276 for agitation of the powder sample 266 in order to produce a cloud of particles in chamber 256, as described above in connection with FIG. 6. Air is supplied through inlet tube 290, space 288 and passages 286 into the periphery of chamber 256 to produce a sheath of air around the wall of chamber 256 flowing toward outlet 260. The air sheath limits deposition of particles on the walls of chamber 256. The cloud of particles is carried downwardly into the lower portion 258 and through the annular shear region defined between outlet 260 and the tapered tip of pin 274. The annular shear region operates as described hereinabove in connection with FIG. 6A to separate clusters of particles and to produce a particle stream consisting essentially of single particles. The particle stream flows through outlet 260 and sample injection tube 262 to the particle size measurement system or other instrument.

It will be appreciated that the powder dispersers shown in FIGS. 6, 8 and 9 all perform the steps of agitating a powder sample to produce a cloud of particles and then carrying the cloud of particles through a shear region where clusters of particles are separated to form a particle stream consisting essentially of single particles.

Another embodiment of beam forming optics for converting laser beam 12 into dual, closely-spaced light beams is illustrated in FIG. 10. The laser beam 12 is focused on a slit aperture 302 in an aperture plate 304 by a cylindrical lens 306. The slit aperture 302 preferably has a width of about 0.1 millimeter and a length of about 3 millimeters and is used as a spatial filter to block off-axis portions of laser beam 12. The slit aperture 302 is preferably located at the focal line of cylindrical lens 306, and the long dimension of slit aperture 302 is parallel to the focal line. The cylindrical lens 306 focuses beam 12 in a direction perpendicular to its focal line, but has little effect on the beam 12 in a direction parallel to its focal line.

The beam diverging from the slit aperture 302 impinges on a cylindrical lens 310. The cylindrical lens 310 is positioned to image the slit aperture 302 at the particle stream 34. A sharp focus is obtained at particle stream 34 when $1/f_{310} = 1/y + 1/x$, where $f_{310}$ is the focal length of cylindrical lens 310, y is the distance between the aperture slit 302 and lens 310, and x is the distance between lens 310 and particle stream 34. Enlarged views of the region in measurement chamber 30 where particle beam 34 intersects the dual light beams are shown in FIGS. 11A and 11B. Cylindrical lens 310 focuses a light beam 312 to form a sharply-focused image 314 where the light beam 312 crosses particle stream 34. The particle stream 34 lies in an imaginary image plane perpendicular to the axis of light beam 312. A cross-section of the image 314 in the image plane is elongated in a direction perpendicular to particle stream 34 and is thin in a direction along particle stream 34, as shown in FIG. 11B.

Referring again to FIG. 10, the beam 312, after passing through particle stream 34, is incident upon a mirror 318 having a concave cylindrical reflecting surface 320. The reflecting surface 320 is arc-shaped in the plane of FIG. 10 and is uniform in cross-section perpendicular to the plane of FIG. 10. The reflecting surface 320 has an axis 322. The mirror 318 is positioned such that axis 322 intersects particle stream 34 and is perpendicular thereto, as shown in FIGS. 11A and 11B. In addition, axis 322 is displaced from the axis of light beam 312 such that the reflection from surface 320 is a light beam 324 that is displaced from light beam 312. Mirror 318 focuses light beam 324 to form an image 326 of aperture slit 302 where the light beam 324 crosses particle stream 34.

The geometry of reflecting surface 320 dictates that image 326 and image 314 are equally displaced from axis 322. Ideally, the reflecting surface 320 should have an ellipsoidal shape with focal points located at the images 314 and 326. However, because of the close spacing between images 314 and 326, typically on the order of 1 millimeter, a concave cylindrical surface 320 is an adequate approximation and is more practical to fabricate. The image 326 has a thin, elongated shape and is parallel to image 314, as shown in FIG. 11B. Preferably, the images 326 and 314 have equal dimensions on the order of about 0.02 millimeters thick by 1 millimeter wide and have a separation of about 1 millimeter.

As discussed hereinabove, the spacing between images 326 and 314 is used to determine particle time of flight. It is sometimes necessary to adjust the spacing to insure accurate measurements under all conditions. In the embodiment of FIG. 10, the spacing between images 326 and 314 can be adjusted by moving mirror 318 along a line parallel to particle stream 34 in a direction indicated by arrow 330 in FIG. 10. Since the beam 312 is fixed in position, movement of the mirror 318 causes the image 326 to move along particle stream 34 relative to image 314. The mirror 318 can be moved in the direction of arrow 330 by any suitable mechanical adjustment means, such as a threaded adjustment screw.

The beam 324, after passing through particle stream 34, is refocused by cylindrical lens 310 in a region near aperture plate 304. Preferably, the beam 324 is absorbed to prevent undesired reflections which otherwise could potentially interfere with measurements in chamber 30. In a preferred embodiment, a prism 332 is positioned near aperture plate 304 for directing beam 324 at a light absorber 334. It will be understood that various light beam absorber configurations can be utilized to prevent undesired reflections.

Another embodiment of the beam forming optics is shown in FIG. 12. The laser beam 12 is focused by a cylindrical lens 350 to form a beam 352. The cylindrical lens 350 is spaced from particle stream 34 by a distance equal to its focal length. At an intersection 354 with particle stream 34, the beam 352 is sharply focused and has a thin, elongated cross-sectional shape. The beam 352, after passing through particle steam 34, impinges on a mirror 358 having a concave cylindrical surface 360. The mirror 358 has generally the same characteristics as the mirror 318, shown in FIG. 10 and described hereinabove. Mirror 358 reflects the beam 352 and focuses it to form a beam 362. The mirror 358 is spaced from particle stream 34 such that the axis of the cylindrical surface intersects and is perpendicular to particle stream 34. At an intersection 364 with particle stream 34, the beam 362 is sharply focused and has a thin, elongated cross-sectional shape. The cylindrical lens 350 shapes the generally round laser beam 12 into a thin, elongated shape, since the beam is focused in only one direction. The second beam is formed by mirror 358 in the same manner as described hereinabove in connection with FIGS. 10, 11A and 11B.

A variation of the beam forming optics of FIG. 10 is shown in FIG. 13, wherein like elements have the same reference numerals. In the embodiment of FIG. 13, the cylindrical mirror is replaced by an optical element 370. The optical element 370 includes a flat reflecting surface 372 and a convex cylindrical lens 374. Preferably, the flat reflecting surface 372 is formed on the flat surface of convex cylindrical lens 374, and the convex surface of lens 374 faces particle stream 34. The lens 374 is spaced from particle stream 34 by a distance equal to the focal length of lens 374 and is slightly offset from the axis of light beam 312. The light beam 312 is sharply focused at particle stream 34 to form image 314. After passing through particle stream 34, the light beam 312 is reflected by surface 372 to form light beam 324. The light beam 324 is sharply focused by lens 374 to form image 326 at particle stream 34. The spacing between images 314 and 326 is established by the offset of lens 374 from the axis of beam 312, and can be adjusted by moving optical element 370 in a direction indicated by arrow 376 parallel to particle stream 34. Generally, the optical element 370 performs the same function as mirror 318, shown in FIG. 10.

In a variation of the optical element 370, the convex surface of cylindrical lens 374 faces away from particle stream 34, and a flat mirror is formed on a separate surface. The mirror is positioned on the opposite side of lens 374 from particle stream 34. Although this configuration operates in the same manner as FIG. 13, it is less practical since a lens and a separate mirror are required.

A further embodiment of the beam forming optics is shown in FIG. 14. The laser beam 12 is directed at a diffraction grating 378. The diffraction grating 378 corresponds to the diffraction grating 116 shown in FIG. 5 and described hereinabove, and is constructed so that most of the input light energy appears in the zero order lobe and one of the first order lobes. In FIG. 14, the diffraction grating 378 is shown as providing a zero order lobe 380 and a first order lobe 382, both of which are directed at a cylindrical lens 384. The cylindrical lens 384 is positioned so as to focus lobes 380 and 382 and to form a pair of beams 386, 388 that are approximately parallel. Each of the beams 386, 388 has a thin, elongated cross-sectional shape. The beams 386, 388 intersect particle stream 34 to permit time-of flight measurement as described hereinabove.

While there has been shown and described what is at present considered the preferred embodiments of the present invention, it will be obvious to those skilled in the art that various changes and modifications may be made therein without departing from the scope of the invention as defined by the appended claims.

What is claimed is:

1. Apparatus for generating closely-spaced first and second light beams in an image plane, each light beam having a thin, elongated cross-sectional shape, comprising:

source means for generating an incident light beam;
  means defining an aperture slit;
  first lens means for focusing the incident light beam on said slit defining means;
  second lens means positioned for focusing an image of said aperture slit in said image plane to form said first light beam; and
  optical means for reflecting said first light beam after passing through said image plane to form a reflected first light beam and for focusing said reflected first light beam in said image plane to form said second light beam spaced from said first light beam.

2. Apparatus as defined in claim 1 wherein said optical means comprises a concave cylindrical mirror having an axis lying in said image plane between said first and second light beams.

3. Apparatus as defined in claim 2 further comprising adjustment means for adjusting the spacing between said first and second light beams, said adjustment means including means for displacing said cylindrical mirror parallel to said image plane in a direction perpendicular to the axis of said cylindrical mirror.

4. Apparatus as defined in claim 1 wherein said second lens means comprises a cylindrical lens.

5. Apparatus as defined in claim 1 wherein said first lens means comprises a cylindrical lens.

6. Apparatus as defined in claim 1 wherein said optical means comprises a flat mirror and a convex cylindrical lens, said lens being spaced from said image plane by a distance equal to its focal length.

7. Apparatus as defined in claim 6 further comprising adjustment means for adjusting the spacing between said first and second light beams, said adjustment means including means for displacing said flat mirror and said cylindrical lens parallel to said image plane in a direction perpendicular to the axis of said cylindrical lens.

8. Apparatus as defined in claim 1 further including means for absorbing said second light beam after passing through said image plane.

9. Apparatus as defined in claim 8 wherein said absorbing means comprises a prism located adjacent to said aperture slit for deflecting said second light beam and a beam absorber for intercepting said second light beam after deflection by said prism.

10. Apparatus as defined in claim 1 wherein said source means comprises a laser.

11. Apparatus for generating closely-spaced first and second light beams in an image plane, each light beam having a thin, elongated cross-sectional shape, comprising:
source means for generating an incident light beam;
a cylindrical lens for focusing said incident light beam in said image plane to form said first light beam; and
optical means for reflecting said first light beam after passing through said image plane to form a reflected first light beam and for focusing said reflected first light beam in said image plane to form said second light beam spaced from said first light beam.

12. Apparatus as defined in claim 11 wherein said optical means comprises a concave cylindrical mirror having an axis lying in said image plane between said first and second light beams.

13. Apparatus as defined in claim 12 further comprising adjustment means for adjusting the spacing between said first and second light beams, said adjustment means including means for displacing said cylindrical mirror parallel to said image plane in a direction perpendicular to the axis of said cylindrical mirror.

14. Apparatus as defined in claim 11 wherein said optical means comprises a flat mirror and a convex cylindrical lens, said lens being spaced from said image plane by a distance equal to its focal length.

15. Apparatus as defined in claim 14 further comprising adjustment means for adjusting the spacing between said first and second light beams, said adjustment means including means for displacing said flat mirror and said cylindrical lens parallel to said image plane in a direction perpendicular to the axis of said cylindrical lens.

16. Apparatus as defined in claim 11 further including means for absorbing said second light beam after passing through said image plane.

17. A method for generating closely-spaced first and second light beams in an image plane, each light beam having a thin, elongated cross-sectional shape, said method comprising the steps of:
generating an incident light beam;
focusing the incident light beam on an aperture slit;
focusing an image of said aperture slit in said image plane to form said first light beam;
reflecting said first light beam after it passes through said image plane to form a reflected first light beam; and
focusing said reflected first light beam in said image plane to form said second light beam spaced from said first light beam.

18. A particle sizing system comprising:
an evacuated measurement chamber;
means for directing a stream of particles to be measured through said measurement chamber;
beam generating means for directing closely-spaced first and second light beams through said particle stream, each light beam having a thin cross-section along the direction of said particle stream and having an elongated cross-section in a direction perpendicular to said particle stream, said beam generating means including
source means for generating an incident light beam,
means defining an aperture slit,
first lens means for focusing the incident light beam on said slit defining means,
second lens means positioned for focusing an image of said aperture slit at said particle stream to form said first light beam, and
optical means for reflecting said first light beam after passing through said particle stream to form a reflected first light beam and for focusing said reflected first light beam at said particle stream to form said second light beam spaced from said first light beam; and
means for measuring particle sizes based on the times of flight of particles in said particle stream between said first light beam and said second beam.

19. A particle sizing system as defined in claim 18 wherein said optical means comprises a concave cylindrical mirror having an axis intersecting said particle stream between said first and second light beams.

20. A particle sizing system as defined in claim 18 wherein said optical means comprises a flat mirror and a convex cylindrical lens, said lens being spaced from said particle stream by a distance equal to its focal length, and the axis of said lens being perpendicular to said particle stream.

21. A particle sizing system as defined in claim 18 further comprising adjustment means for adjusting the spacing between said first and second light beams, said adjustment means including means for displacing said optical means along a line parallel to said particle stream.

22. Apparatus for generating closely-spaced first and second light beams in an image plane, each light beam having a thin, elongated cross-sectional shape, comprising:
source means for generating an incident light beam;
a diffraction grating positioned to convert a portion of the incident light beam into diffracted beams in a zero order lobe and at least one first order lobe; and a cylindrical lens spaced from said diffraction grating for focusing said zero order lobe and said at least one first order lobe into said first and second light beams, respectively, said cylindrical lens being spaced from said diffraction grating such that said first and second light beams are substantially parallel.

* * * * *